United States Patent [19]

Jameson

[11] Patent Number: 5,584,989
[45] Date of Patent: Dec. 17, 1996

[54] APPARATUS FOR SUPERCRITICAL FLUID EXTRACTION HAVING MEANS FOR REMOVING EXTRACTION FROM COLLECTION SOLVENT

[75] Inventor: Daniel G. Jameson, Lincoln, Nebr.

[73] Assignee: Isco, Inc., Lincoln, Nebr.

[21] Appl. No.: 134,032

[22] Filed: Oct. 12, 1993

Related U.S. Application Data

[60] Division of Ser. No. 26,998, Mar. 5, 1993, Pat. No. 5,269,930, which is a continuation-in-part of Ser. No. 908,458, Jul. 6, 1992, Pat. No. 5,198,197, which is a division of Ser. No. 795,987, Nov. 22, 1991, Pat. No. 5,160,624, which is a continuation-in-part of Ser. No. 553,119, Jul. 13, 1990, Pat. No. 5,094,753.

[51] Int. Cl.$^6$ .................................................. B01D 11/04
[52] U.S. Cl. ........................ 210/137; 96/155; 210/188; 210/511; 210/634; 422/69; 422/103; 422/256
[58] Field of Search .................................. 210/137, 511, 210/634, 188, 198.2, 656, 808; 422/103, 255, 256, 260, 261, 288, 69, 70; 96/155, 174

[56] References Cited

U.S. PATENT DOCUMENTS

| 524,702 | 8/1894 | Browning . |
| 2,507,851 | 5/1950 | Bryant et al. . |
| 2,955,916 | 10/1960 | Guyer et al. ........................... 422/288 |

(List continued on next page.)

FOREIGN PATENT DOCUMENTS

| 124686 | 10/1967 | Czechoslovakia . |
| 438184A1 | 1/1988 | European Pat. Off. . |
| 275933A2 | 7/1988 | European Pat. Off. . |
| 416326A2 | 3/1991 | European Pat. Off. . |
| 458125A3 | 5/1991 | European Pat. Off. . |
| 450182A2 | 10/1991 | European Pat. Off. . |

(List continued on next page.)

OTHER PUBLICATIONS

Wright, B. W., et al., 1987, "Analytical Supercritical Fluid Extraction of Adsorbent Materials", Anal. Chem., 59:38–44.

Sugiyama, K., et al., 1985, "New Double–Stage Separation Analysis Method: Directly Coupled Laboratory–Scale Supercritical Fluid Extraction–Supercritical Chromatography, Monitored With A Multiwavelength Ultraviolet Detector", J. Chromatog., 332:107–116.

Hawthorne, S. B., et al., 1986, "Extraction and Recovery of Organic Pollutants from Environmental Solids and Tenax–GC Using Supercritical $CO_2$", J. Chromatog. Science, 24:258–264.

Hawthorne, S. B., et al., 1987, "Extraction and Recovery pf Polycyclic Aromatic Hydrocarbons from Environmental Solids Using Supercritical Fluids", Anal. Chem., 59:1705–1708.

Schantz, M. M., et al., 1986, "Supercritical Fluid Extraction Procedure for the Removal of Trace Organic Species from Solid Samples", J. Chromatogr., 363:397–401.

(List continued on next page.)

Primary Examiner—Joseph W. Drodge
Attorney, Agent, or Firm—Vincent L. Carney

[57] ABSTRACT

To collect analyte in a supercritical fluid extraction process, the extractant flows to a collection container under pressure. In one embodiment, the collection container contains collection solvent through which the extractant flows to partition analyte. The extractant adds to the liquid and when the collection solvent-extractant mixture rises to a heating zone, the extractant vaporizes seleclively since its vapor pressure is higher than the vapor pressure of the collection solvent. When its pressure exceeds a preset valve pressure it is vented so that extractant continually leaves the collection container. After the extraction is complete, the analyte is concentrated in the collection solvent. In another embodiment, the collection vessel includes a solid material on which the analyte collects. It is removed under pressure by a solvent that is concentrated under pressure.

4 Claims, 2 Drawing Sheets

U.S. PATENT DOCUMENTS

| | | |
|---|---|---|
| 3,198,948 | 8/1965 | Olson . |
| 3,257,561 | 6/1966 | Packard et al. . |
| 3,872,723 | 3/1975 | Busch . |
| 4,032,445 | 6/1977 | Munk . |
| 4,064,908 | 12/1977 | Loe . |
| 4,217,931 | 8/1980 | Jackel . |
| 4,225,290 | 9/1980 | Allington et al. . |
| 4,265,860 | 5/1981 | Jennings et al. . |
| 4,375,163 | 3/1983 | Yang . |
| 4,476,732 | 10/1984 | Yang . |
| 4,477,266 | 10/1984 | Yang . |
| 4,483,773 | 11/1984 | Yang . |
| 4,564,145 | 1/1986 | Takada et al. . |
| 4,597,943 | 7/1986 | Sugiyama et al. . |
| 4,676,897 | 6/1987 | Kuze et al. . |
| 4,705,459 | 11/1987 | Buisine et al. . |
| 4,711,764 | 12/1987 | Good . |
| 4,714,591 | 12/1987 | Avedesian ............................... 422/256 |
| 4,770,780 | 9/1988 | Moses ..................................... 210/634 |
| 4,820,129 | 4/1989 | Magnussen . |
| 4,851,683 | 7/1989 | Yang . |
| 4,913,624 | 4/1990 | Seki . |
| 4,915,591 | 4/1990 | Funke . |
| 4,962,275 | 10/1990 | Bruno ..................................... 210/634 |
| 4,984,602 | 1/1991 | Saito et al. . |
| 5,013,443 | 5/1991 | Higashidate et al. . |
| 5,073,267 | 12/1991 | Adda et al. ............................. 210/634 |
| 5,075,017 | 12/1991 | Hossain et al. . |
| 5,087,360 | 2/1992 | Wright et al. ........................... 210/634 |
| 5,094,741 | 3/1992 | Frank et al. ............................ 210/634 |
| 5,133,859 | 7/1992 | Frank et al. . |
| 5,147,538 | 9/1992 | Wright et al. . |
| 5,151,178 | 9/1992 | Nickerson et al. . |
| 5,164,693 | 11/1992 | Yokoyama et al. . |
| 5,178,767 | 1/1993 | Nickerson et al. . |
| 5,180,487 | 1/1993 | Saito et al. . |
| 5,198,197 | 3/1993 | Clay et al. . |
| 5,205,987 | 4/1993 | Ashraf-Khorassani et al. . |
| 5,240,603 | 8/1993 | Frank et al. . |
| 5,253,981 | 10/1993 | Yang . |
| 5,271,903 | 12/1993 | Durst et al. ............................ 210/511 |
| 5,322,626 | 6/1994 | Frank et al. . |

FOREIGN PATENT DOCUMENTS

| | | |
|---|---|---|
| 458125A2 | 11/1991 | European Pat. Off. . |
| 466291A3 | 1/1992 | European Pat. Off. . |
| 558172A2 | 9/1993 | European Pat. Off. . |
| 595443A1 | 4/1994 | European Pat. Off. . |
| 41424 | of 0000 | Hungary . |
| 58-38115 | of 0000 | Japan . |
| 58-9317 | of 0000 | Japan . |
| 63-56425 | of 0000 | Japan . |
| 64-44847 | of 0000 | Japan . |
| 3-251435 | of 0000 | Japan . |
| 2-8039 | of 0000 | Japan . |
| 3-26531 | of 0000 | Japan . |
| 1129003 | 6/1986 | Japan ..................................... 422/256 |
| 463644 | 3/1975 | U.S.S.R. . |
| 1552201 | 9/1979 | United Kingdom . |
| WO82/01578 | 5/1982 | WIPO . |
| WO85/04816 | 11/1985 | WIPO . |
| WO92/06058 | 4/1992 | WIPO . |
| WO94/20190 | 9/1994 | WIPO . |
| WO95/03106 | 2/1995 | WIPO . |

OTHER PUBLICATIONS

Wright, B. W., et al., 1989, "Supercritical Fluid Extraction of Coal Tar Contaminated Soil Samples", Energy & Fuels, 3:474–480.

Lee, M. L., et al., 1979, "Retention Indices for Programmed–Temperature Capillary–Column Gas Chromatography of Polycyclic Aromatic Hydrocarbons", Anal. Chem., 51(6):768–774.

Vassilaros, D. L., et al., 1982, "Linear Retention Index System For Polycyclic Aromatic Compounds", J. Chromatogr., 252:1–20.

Czubryt, J. J., et al., 1970, "Solubility Phenomena in Dense Carbon Dioxide Gas in the Range 270–1900 Atmospheres", J. Phys. Chem., 74(24):4260–4266.

Wise, S. A., et al., 1988, "Determination of Polycyclic Aromatic Hydrocarbons in a Coal Tar Standard Reference Material", Anal. Chem., 60:887–894.

Villaume, J. F., 1984, "Coal Tar Wastes: Their Environmental Fate and Effects", *Hazardous and Toxic Wastes: Technology, Management, and Health Effects*, Chapter 25, S. K. Majumdar and E. W. Miller, Eds., pp. 362–375.

Maxwell, R. J., et al., 1992, "Improved SFE Recovery of Trace Analytes from Liver Using an Intergral Micrometering Valve–SPE Column Holder Assembly", J. High Resolution Chromatogr., 15:807–811.

Levy, J. M., et al., 1990, "Qualitative Supercritical Fluid Extraction Coupled to Capillary Gas Chromatography", J. High Resolution Chromatogr., 13:418–421.

Levy, J. M., et al., 1991, "The Use of Alternative Fluids in On–Line Supercritical Fluid Extraction–Capillary Gas Chromatography", J. High Resolution Chromatogr., 14:661–668.

Wright, B. W., et al., 1992, "Evaluation of a Field–Portable Supercritical Fluid Extraction Apparatus for Rapid Characterization of Contaminated Soils", *Waste Testing and Quality Assurance: Third Volume*, D. Friedman, Eds., pp. 3–14.

Richter, B. E., 1985, "Modified Flame Ionization Detector for the Analysis of Large Molecular Weight Polar Compounds by Capillary Supercritical Fluid Chromatography", J. High Resolution Chromatogr. & Chromatogr. Communications, 8:297–300.

Daimon, H., et al., 1991, "Directly Coupled Supercritical–Fluid Extraction/Capillary Supercritical–Fluid Chromatography of Polymer Additives", Chromatographia, 32:549–554.

Levy, J. M., et al., 1989, "Quantitative Supercritical Fluid Extraction Coupled to Capillary Gas Chromatography", Chromatographia, 28:613–616.

Nielen, M. W. F., et al., 1989, "On–line System for Supercritical Fluid Extraction and Capillary Gas Chromatography with Electron–Capture Detection", J. Chromatog., 474:388–395.

Raynor, M. W., et al., 1988, "Supercritical Fluid Extraction/Capillary Supercritical Fluid Chromatography/Fourier Transform Infrared Microspectrometry of Polycyclic Aromatic Compounds in a Coal Tar Pitch", J. High Resolution Chromatog. & Chromatog. Communications, 11:766–775.

Hawthorne, S. B., et al., 1989, "Coupled SFE–GC: A Rapid and Simple Technique for Extracting, Identifying, and Quantitating Organic Analytes from Solids and Sorbent Resins", J. Chromatog. Science, 27:347–354.

Berger, T. A., et al., 1989, "Linear Velocity Control in Capillary Supercritical Fluid Chromatography by Restrictor Temperature Programming", J. Chromatog., 465:157–167.

Lipsky, S. R., et al., 1986, "High Temperature Gas Chromatography: The Development of New Aluminum Clad Flexible Fused Silica Glass Capillary Columns Coated with Thermostable Nonpolar Phases: Part 1", J. High Resolution Chromatog. & Chromatog. Communications, 9:376–382.

Green, S., et al., 1988, "Simple Restrictors for Capillary Column Supercritical Fluid Chromatography", J. High Resolution Chromatog. & Chromatog. Communications, 11:414–415.

Raynor, M. W., et al., 1988, "Preparation of Robust Tapered Restrictors for Capillary Supercritical Fluid Chromatography", J. High Resolution Chromatog. & Chromatog. Communications, 11:289–291.

Jinno, K., et al., 1991, "Coupling of Supercritical Fluid Extraction with Chromatography", Anal. Sci., 7:361–369.

Jentoft, R. E., et al., 1972, "Apparatus for Supercritical Fluid Chromatography with Carbon Dioxide as the Mobile Phase", Anal. Chem., 44:681–686.

Campbell, R. M., et al., 1986, "Supercritical Fluid Fractionation of Petroleum– and Coal–Derived Mixtures", Anal. Chem., 58:2247–2251.

Nam, K. S., et al., 1990, "Supercritical Fluid Extraction and Cleanup Procedures for Determination of Xenobiotics in Biological Samples", Chemosphere, 20:873–880.

Campbell, R. M., et al., 1989, "Supercritical Fluid Extraction of Chlorpyrifos Methyl from Wheat at Part per Billion Levels", J. Microcolumn Separations, 1:302–308.

Onuska, F. I., et al., 1989, "Supercritical Fluid Extraction of 2,3,7,8–Tetrachlorodibenzo–p–dioxin from Sediment Samples", J. High Resolution Chromatog., 12:357–361.

Aida, T., et al., "Organic Chemistry in Supercritical Fluid Solvents: Photoisomerization of trans–Stilbene", ACS Symposium Series 329, *Supercritical Fluids: Chemical and Engineering Principles and Applications*, T. G. Squires and M. E. Paulaitis, Eds., American Chemical Society, Chapter 5, pp. 58–66.

Barber, T. A., et al., 1990, "Solubility of Solid $Ccl_4$ in Supercritical $CF_4$ Using Directly Coupled Supercritical Fluid Extraction–Mass Spectrometry", Separation Science and Technology, 25:2033–2043.

Bond, N. D., 1981, "H–Coal Pilot Plant High Pressure and Temperature Letdown Valve Experience", Proc.of the 1981 Symposium on Instrumentation and Control for Fossil Energy Processes, Argonne National Lab. Report ANL 81–62, Jun. 8–10, pp. 654–679.

Bowman, L. M., 1976, "Dense Gas–Chromatographic Studies", Dissertation, Chapter 3, pp. 35–42.

Driskell, L., 1876, "Coping with High–Pressure Letdown", Chemical Engineering, 83:113–118.

Gardner, J. F., 1980, "Critical Valve Specifications and METC Valve–Testing Projects", Proc. of the 2nd Symposium on Valves for Coal Conversion and Utilization, DOE/MC/14522–1, Sec. 19.

Giddings, J. C., et al., 1977, "Exclusion Chromatography in Dense Gases: An Approach to Viscosity Optimization", Anal. Chem., 49:243–249.

Grancher, et al., 1973, "The SNPA–DEA Process for the Desulfurization of High Pressure Gases", Proc. of the International Conference on Control of Gaseous Sulphur Compound Emission, Apr. 10–12.

Hartmann, W., et al., 1977, "Fluid Chromatography of Oligomers", Proc. of the 6th AIRAPT International High Pressure Conference, *High–Pressure Science and Technology*, K. D. Timmerhaus and M. S. Barber, Eds., pp. 573–582.

Hawthorne, S. B., et al., 1990, "Quantitative Analysis Using Directly Coupled Supercritical Fluid Extraction–Capillary Gas Chromatography (SFC–GC) With a Conventional Split/Splitless Injection Port", J. Chromatogr. Science, 28:2–8.

Hawthorne, S. B., et al., 1987, "Directly Coupled Supercritical Fluid Extraction–Gas Chromatographic Analysis of Polycyclic Aromatic Hydrocarbons and Polychlorinated Biphenyls from Environmental Solids", J. Chromatogr., 403:63–76.

Hirata, Y., et al., 1989, "Supercritical Fluid Extraction Combined with Microcolumn Liquid Chromatography for the Analysis of Polymer Additives", J. Microcolumn Separations; vol. 1, No. 1, 1989, pp. 46–50.

Illing, H. H., 1982, "Design Principles of Low Impingement Type Slurry Letdown Valves", Proc. of the 1982 Symposium on Instrumentation and Control for Fossil Energy Processes, Argonne National Lab. Report ANL 82–62, pp. 461–468.

Klesper, E., 1978, "Chromatography with Supercritical Fluids", Angew. Chem. Int. Ed. Eng., 17:738–746.

Klesper, E., et al., 1978, "Apparatus and Separations in Supercritical Fluid Chromatography", European Polymer Journal, 5:77–88.

Lapple, C. E., 1943, "Isothermal and Adiabatic Flow of Compressible Fluids", Trans. American Institute of Chemical Engineers, 39:385–432.

Liepmann, H. W., et al., 1957, "Flow in Ducts and Wind Tunnels", *Elements of Gasdynamics*, Chapter 5, pp. 124–143.

I. Moradinia, et al., 1987, "Solubilities of Five Solid n–Alkanes in Supercritical Ethane", ACS Symposium Series 329, *Supercritical Fluids*, T. G. Squires and M. E. Paulaitis, Eds., American Chemical Society, Chapter 11, pp. 130–137.

Nair, J. B., et al., "On–Line Supercritical Sample–Preparation Accessory for Chromatography", LC–GC, 6:1071–1073.

Nilsson, W. B., et al., 1989, "Supercritical Fluid Carbon Dioxide Extraction in the Synthesis of Trieicosapentaenoylglycerol from Fish Oil", ACS Symposium Series 406, *Supercritical Fluid Science and Technology*, K. P. Johnston and J. M. L. Penninger, Eds., Chapter 5, pp. 89–108.

Platt, R. J., 1981, "High–Pressure Slurry–Letdown Valve Designs for Exxon Coal–Liquefaction Pilot Plant", Proc. Of the 2nd Symposium on Valves for Coal Conversion and Utilization, DOE/MC/14522–1, Sec. 6.

Rizvi, et al., 1988, "Concentration of Omega–3 Fatty Acids from Fish Oil Using Supercritical Carbon Dioxide", ACS Symposium B. A. Charpentier and M. R. Sevenants, Eds., Chapter 5, pp. 89–108.

Saito, M., et al., "Fractionation by Coupled MicroSupercritical Fluid Extraction and Supercritical Fluid Chromatography", (Royal Soc. Chem. Chromatography Monographs), *Supercritical Fluid Chromatography*, R. M. Smith, 1988, Chapter 8, pp. 203–230.

Saito, M., et al., 1989, "Enrichment of Tocopherols in Wheat Germ by Directly Coupled Supercritical Fluid Extraction with Semipreparative Supercritical Fluid Chromatography", J. Chromatogr. Sci., 27:79–85.

Smith, R. D., et al., 1986, "Performance of Capillary Restrictors in Supercritical Fluid Chromatography", Anal. Chem., 58:2057–2064.

Temelli, F., et al., 1988, "Supercritical Carbon Dioxide Extraction of Terpenes from Orange Essential Oil", ACS Symposium Series 366, *Supercritical Fluid Extraction and Chromatography*, B. A. Charpentier and M. R. Sevenants, Eds., Chapter 6, pp. 109–126.

Wright, B. W., et al., 1988, "Analytical Supercritical Fluid Extraction Methodologies", ACS Symposium Series 366, *Supercritical Fluid Extraction and Chromatography*, B. A. Charpentier and M. R. Sevenants, Eds., Chapter 3, pp. 44–62.

Conoflow Corp. Valve Catalog sheets for 1968 and 1969.

Greibrokk, T., et al., 1984, "New System for Delivery of the Mobile Phase in Supercritical Fluid Chromatography", *Anal. Chem.*, 56:2681–2684.Wheeler, J. R., et al., "Is SFC Worth the Effort?", *Res. & Dev.;* Chromatography; Feb.:134–138.

Hirata, Y., et al., "Direct Sample Injection in Supercritical Fluid Chromatography with Packed Fused Silica Column", *Journal of High Resolution Chromatography & Chromatography Communications*, vol. 11, Jan. 1988; pp. 81–84.

Berger, T. A., et al., "A New Supercritical Fluid Chromatograph", Paper 255, HPLC–92, 16th International Symposium on Column Liquid Chromatography, Lafayette, IN.

Thiebaut, D., et al., "Supercritical–Fluid Extraction of Aqueous Samples and On–Line Coupling to Supercritical–Fluid Chromatography", *On–Line Coupling to SFE and SFC*, 1989 Elsevier Science Publishers B.V.; pp. 151–159.

Wheeler, J. R., et al., "Supercritical Fluid Extraction and Chromatography of Representative Agricultural Products with Capillary and Microbore Columns", *Journal of Chromatographic Science*, vol. 27, Sep. 1969; pp. 534–539.

Lopez–Avila, Viorica, et al., "SFE/IR Method for the Determination of Petroleum Hydrocarbons in Soils and Sediments", Environmental Monitoring Systems Laboratory, Contract No. 68–C1–0029, Section 4, p. 8.

Levy, Joseph M., et al., "Multidimensional Supercritical Fluid Chromatography and Supercritical Fluid Extraction", *Journal of Chromatographic Science*, vol. 27, Jul. 1989, pp. 341–346.

Schwartz, H. E., et al., "Gradient Elution Chromatography with Microbore Columns", *Analytical Chemistry*, vol. 55, No. 11, Sep., 1983, pp. 1752–1760.

Schwartz, H. E., et al., "Comparison of Dynamic and Skate Mixing Devices for Gradient Micro–HPLC", *Journal of Chromatographic Science*, vol. 23, Sep., 1985, pp. 402–406.

SFE–Plus Supercritical Fluid Extraction System brochure, Micro–Tech Scientific.

Kalinoski, Henry T., et al., "Supercritical Fluid Extraction and Direct Fluid Injection Mass Spectrometry for the Determination of Trichothecene Mycotoxins in Wheat Samples", *Anal. Chem.* 1986, 58, 2421–2422.

Ramsey, Edward D., et al., "Analysis of Drug Residues in Tissue by Combined Supercritical–Fluid Extraction–Supercritical–Fluid Chromatography–Mass Spectrometry–Mass Spectrometry", *Journal of Chromatography*, 464 (1989) 353–357.

Sims, Marc, et al., "Design and Control of CO2 Extraction Plants", presented at 2nd International Symposium on Supercritical Fluids, May 20–22, 1991, Boston, MA; pp. 1–8.

Lack, E., et al., "Findings and Experience Acquired in Operating Industrial High Pressure Extraction Plants with Supercritical CO2", pp. 473–480.

Engineered Pressure Systems Inc. "Supercritical Fluid Extraction" brochure.

SITEC brochure on HP–Spray Drying/Micronisation/Supercritical Extraction and pilot plants.

Brochure from Extract Company GMBH on "Extraction with supercritical gases" production plants.

Brochure "Hochdruck–Extraktion—$CO_2$" from UHDE.

Korner, J. P., "New Developments in the Design and Construction of Industrial–size SCGE Plants", Proceedings of the International Symposium on Supercritical Fluids, Tome 1, Nice France, Oct. 17, 18, 19, 1988; pp. 633–641.

"Instruments for Separation and Analysis" Product Guide 12, Isco, Inc., Brochure 9501, Jan. 1995.

Suprex Corporation brochure "MPS/225".

Specs for Chassis for Ultra Plus Extrapolator by Micro–Tech Scientific, by F. Yang, Sep. 1994.

Yang, F. J., et al., "Design Concepts for a New Generation Supercritical Fluid Extraction System", Micro–Tech Scientific.

McNally, Mary Ellen P., et al., "Supercritical Fluid Extraction Coupled with Supercritical Fluid Chromatography for the Separation of Sulfonylurea Herbicides and their Metabolites from Complex Matrices", *Journal of Chromatography*, 435 (1988) 64–66.

Hawthorne, Steven, et al., "Analysis of Flavor and Fragrance Compounds Using Supercritical Fluid Extraction Coupled with Gas Chromatography", *Anal. Chem.*, 1988, 60, 472–473.

Marc Sims S–F–E brochure on "Dense Gas Management System for Supercritical Fluid Extraction and Processing".

Cassat, D., et al., "Extraction of PCB from Contamined Soils by Supercritical $CO_2$", International Symposium on Supercritical Fluids, Tome 2, Nice France, Oct. 17, 18, 19, 1988, pp. 771–776.

De Ruiter, C., et al., "Design and Evaluation of a Sandwich Phase Separator for On–Line Liquid/Liquid Extraction", *Analytica Chimica Acta*, 192(1987) pp. 267–275.

Advertisement "SFE Analyser 3000", Fisons Instruments SpA; LPI Mar./Apr. 1993.

"RIA" Bulletin 7250, Beckman Instruments.

"Concept 4" brochure; Micromedic Systems.

"The HP 7680A Supercritical Fluid Extractor" brochure; Hewlett–Packard.

37 Supercritical Fluid (Dense Gas) Chromatography/Extraction with Linear Density Programming" Lyle M. Bowman, Jr., Marcus N. Myers, and J. Calvin Giddings; *Separation Science and Technology*, 17(1) (1982) 271–287.

"Microscale Supercritical Fluid Extraction and Coupling of Microscale Supercritical Fluid Extraction with Supercritical Fluid Chromatography" Muneo Saito, Toshinobu Hondo, Masaaki Senda, *Progress in HPLC* vol. 4 (1989) Yoshioka, et al. (Eds) pp. 87–110.

"Fractionation of Anhydrous Milk Fat by Superficial Carbon Dioxide" by Joseph Arul, Armand Boudreau, Joseph Makhlouf, Rene Tardif, and Madhu R. Sahasrabudhe, *Journal of Food Science* vol. 52, No. 5, 1987, pp. 1231–1236.

"Grobtechnische Anlagen zur Extraktion mit uberkritischen Gasen" Von R. Eggers; *Angew. Chem.* 90, 1978, pp. 799–802.

"New Pressure Regulating System for Constant Mass Flow Supercritical–Fluid Chromatography and Physico–Chemical Analysis of Mass–Flow Reduction in Pressure Programming by Analogous Circuit Model" by M. Saito, et al.; *Chromatographia* vol. 25, No. 9, Sep. 1988, pp. 801–805.

APPARATUS FOR SUPERCRITICAL FLUID EXTRACTION HAVING MEANS FOR REMOVING EXTRACTION FROM COLLECTION SOLVENT

RELATED CASES

This application is a division of application Ser. No. 08/026,998, filed Mar. 5, 1993, now U.S. Pat. No. 5,269,930, which is a continuation-in-part application of U.S. application Ser. No. 07/908,458 filed Jul. 6, 1992, now U.S. Pat. No. 5,198,197, which is a division of U.S. application Ser. No. 07/795,987, filed Nov. 22, 1991, now U.S. Pat. No. 5,160,624 which is a continuation-in-part of U.S. application Ser. No. 07/553,119, filed Jul. 13, 1990, now U.S. Pat. No. 5,094,753 for APPARATUS AND METHOD FOR SUPERCRITICAL FLUID EXTRACTION.

BACKGROUND OF THE INVENTION

This invention relates to supercritical fluid extraction.

In supercritical fluid extraction, an extraction vessel is held at a temperature above the critical point and is supplied with fluid at a pressure above the critical pressure. Under these conditions, the fluid within the extraction vessel is a supercritical fluid. In one type of apparatus for supercritical extraction, there is a specially constructed extraction vessel within a source of heat.

A prior art apparatus for supercritical extraction of this type is described by B. W. Wright, et. al., in *ANAL. CHEM.* 59, 38–44 (January 1987) using a glass-lined extraction chamber within a bolted stainless steel extraction vessel heated in an oven. This type of extraction apparatus has the disadvantages of: (1) requiring time consuming steps to open the pressurized extraction vessel before use to insert the sample and again to open it after use to remove the spent sample; and (2) under some circumstances, requiring the handling of a hot extraction vessel.

In some supercritical fluid extraction apparatuses, extractant is collected under pressure in a cold trap. One such prior art device is described in "Supercritical Fluid Fractionation of Petroleum and Coal-Derived Mixtures" *Anal. Chem.* 1986, Vol. 58, pp. 2247–2255. This publication describes extracting under pressure to control the solvating power of the extractant and collecting under pressure. However, for very volatile compounds, this apparatus was reported to be unsuccessful and the extractant was bubbled through a collecting solvent while venting through Teflon tubing. It has a disadvantage in not solvating the extract in a solvent under a controlled adjustable pressure and temperature continuously during the extraction.

Another prior art collection technique is disclosed in Nam, Kapila, Yanders, and Puri, Chemosphere 20, No. 7–9, 873–880 (1990). In this technique, extract is collected under pressure and all the extract from a given extraction is collected in a vessel. Nam, et al. describe no provision for controlled vaporization of the extraction solvent to keep the fluid level constant.

The system described by Nam, et al. has several disadvantages, such as for example: (1) it does not provide for continual feed; and (2) it requires that the collection vessel be large enough to contain the total volume of extraction solvents used, plus any collection solvent, and the extracts extracted.

Usually, the volume of extraction solvent is many times the volume of analyte and the volume of collection solvent in which the analyte is to be concentrated. The volume for extraction solvent required may not be known until a test extraction is done. Fluid volumes are likely to be different between different extraction methods. For these reasons, it is desirable to evaporate the extraction solvent throughout the extraction using a collection vessel volume chosen to accommodate the analyte and collection solvent rather than the volume of extraction solvent.

SUMMARY OF THE INVENTION

Accordingly, it is an object of the invention to provide a novel supercritical extraction technique.

It is a still further object of the invention to provide a novel supercritical extraction apparatus.

It is a still further object of the invention to provide a novel supercritical extraction collection apparatus that improves trapping efficiency by controlling the temperature and pressure of the collection vial.

It is a still further object of the invention to provide a novel supercritical extraction collection apparatus that reduces collection solvent loss by controlling the temperature and pressure of the vial.

It is a still further object of the invention to provide a novel supercritical extraction apparatus that maintains a desirable level in the collection vials during extraction or after the extraction is complete.

It is an object of the invention to provide a novel and efficient collecting trap for the purpose of trapping extracted substances.

It is an object of the invention to provide a novel collecting trap using reduced temperature for the purpose of trapping extracted substances but able to avoid plugging.

It is an object of the invention to provide a novel collecting trap using reduced temperature for the purpose of trapping extracted substances but which nonetheless operates efficiently.

It is an object of the invention to provide a novel capillary tubing outlet end thermally insulated from the surrounding collection solvent into which it is immersed.

It is a still further object of the invention to provide a novel method and apparatus to control the rate of extraction solvent vaporization and the fluid level in a pressurized collection vessel.

It is a still further object of the invention to provide a novel method and apparatus for making an optimal separation of extraction solvent from the analyte and collection solvent.

In accordance with the above and further objects of the invention, a supercritical fluid extraction system includes a cartridge capable of holding the sample to be extracted, a pressure vessel into which the cartridge fits and a pumping system. The pressure vessel fits into a heater and the cartridge is removably mounted to a breech plug that seals the pressure vessel. There are separate outlets for the cartridge and pressure vessel to permit equalization of pressure on the inside and outside of the cartridge without contamination from impurities outside the cartridge but inside the pressure vessel.

For extraction, the cartridge includes an outlet that cooperates with an extractant outlet of the pressure vessel and is connected to the fraction collector so that supercritical fluid flows into the cartridge, out of a fitting that communicates with the interior of the cartridge and into an appropriate collection container containing a collection solvent. The extractant carries the extract from the cartridge into the collection solvent.

Trapping efficiency and low collection solvent losses can be gained by several techniques. One such technique requires reduced collection solvent temperature during extraction on the order of 5 degrees Centigrade or less. However, reduced temperature, while improving trapping and reducing losses, may also create problems with restrictor plugging and icing up of the vial. Ice on the outside of a vial may interfere with the vial being lowered into the vial rack after collection. To prevent these problems, heat must be supplied to the vial to maintain a minimum temperature. Ideally, a system would precool the vial before the extraction begins and then add heat to maintain this temperature.

To improve trapping and reduce losses, a sealed system is used with a regulator to maintain pressure and the collection vials are pressurized sufficiently to reduce the mist and vapors resulting from the violent expansion of the gas exiting the restrictor in an unpressurized vial and to prevent loss of gas through the vial's vent. The pressure is sufficiently elevated to decrease the vaporization rate of collection solvent and extract, so that at a given mass flow rate of gas, the gas volume and bubble size are reduced. In the sealed system, the gases and vapors may be routed for proper and safe disposal.

To maintain an adequate solvent level, a liquid level control system is provided. In one embodiment, the vapor pressure of fluid in the collection vessel is increased when the liquid level increases. This increases the pressure. When the pressure reaches a set point, a back-pressure controlled vent releases vapor and channels to a disposal container. In another embodiment, the level is optically sensed and heat is provided when the level increases beyond a predetermined level. The increased pressure enhances collection, and since their is normally a large amount of extractant, the removal of extractant at a predetermined pressure maintains both the level of liquid and the pressure in a desirable range.

For this purpose, the extractant and collection solvent are selected so that extractant is principally vaporized from the collection solvent-extractant mixture in the collection vessel. The collection solvent and extractant are both selected to operate at a pressure and temperature that permits partition of the extract between the collection solvent and the extractant and avoids deposition and condensation on the walls of the means for supplying fluid to the collection vessel.

After collection, the sample cartridge may be removed from the pressure vessel containing it and a new one inserted. The collection vessel may be used to concentrate the extract under different conditions suitable for the nature of the extract and collection solvent.

As can be understood from the above description, the supercritical extraction technique has several advantages, such as for example: (1) it automates the sample injection and fraction collection part of the extraction process as well as automating the extraction itself; (2) it allows the vials to be changed during the extraction process without depressurizing the extraction chamber; (3) it provides good trapping efficiency; (4) it provides low extract/solvent losses; (5) it provides reduced freezing and plugging of the restrictor; (6) it reduces icing up of the outside of the vial; (7) it permits the conditions of the extraction, such as temperature and pressure, to be changed such as to remove certain substances from the sample matrix and deposit each substance in a separate vial; and (8) it is useful for investigating extraction kinetics by changing the vial during the extraction for examination.

More specifically, this technique has the advantages of: (1) minimizing the decrease of the solvent power which prevents analyte loss in the transfer step by transferring the extraction solvent mixed with analyte to the collection vessel under pressure; (2) minimizing evaporation loss of the analyte and collection solvent if present by separating the extraction solvent from the analyte or analyte plus collection solvent by fractional evaporation; (3) enabling volatile collection solvents to be used without a need for collection solvent replenishment during the extraction; (4) reducing the size of the gas bubbles which form as the extraction solvent expands and thus causing boiling to be less violent by fractional evaporation under pressure; (5) permitting in one embodiment, transfer of the extract to a collection vessel without passing it through a restrictor because only the evaporated extraction solvent, and in some cases evaporated collection solvent, passes through a pressure release or restrictive element and the extraction solvent is maintained at extraction conditions throughout the transfer step so as to prevent restrictor plugging and simplify the restrictor design with no need for restrictor heating.

DESCRIPTION OF THE DRAWINGS

The above noted and other features of the invention will be better understood from the following detailed description when considered with reference to the accompanying drawings, in which.

DETAILED DESCRIPTION

Figure 1:
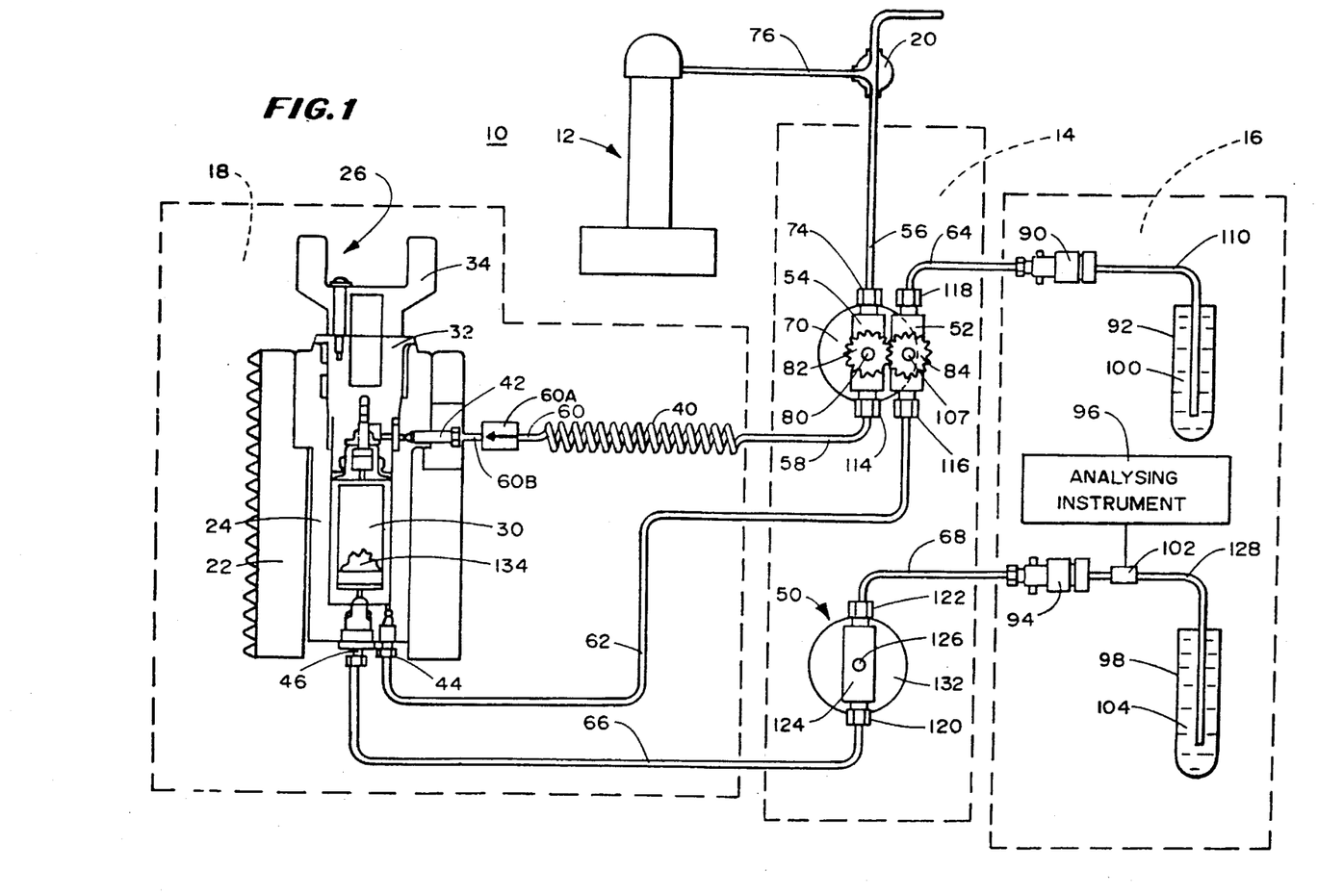
FIG. 1 is a schematic diagram illustrating the operation of a single supercritical fluid extraction system according to the invention.

In FIG. 1, there is shown a schematic fluidic diagram of one channel of a dual-channel supercritical fluid extraction system 10 having a pumping system 12, a valve system 14, a collector system 16 and a pressure vessel and fluid-extraction assembly 18. The pumping system 12 communicates with two extraction cartridges within the pressure vessel and fluid-extraction assembly 18 and for this purpose is connected through a tee joint 20 to two identical valve systems, one of which is shown at 14. Each valve system communicates with a different one of two inlets for the corresponding one of two extraction cartridges.

The valve system 14 and a second valve system (not shown in FIG. 1) which is connected to the other branch of the tee joint 20 are each connected to two different collector systems 16, one of which is shown in FIG. 1, and to different ones of the two extraction cartridges in the pressure-vessel and fluid-extraction assembly 18 so that, two extraction operations can be performed at the same time using the same pumping system 12. With this arrangement, the valve system 14 causes: (1) supercritical fluid to flow from the pumping system 12 into a space between a cartridge and the interior of the pressure vessel of the pressure-vessel and fluid-extraction assembly 18 for purging the outside of the cartridge and the inside of the pressure vessel; and (2) applies supercritical fluid through the cartridge for extraction of a sample 134 therein. Because the fluid is applied both to the interior of the cartridge and the exterior, the cartridge does not have to withstand a high pressure difference between its interior and exterior and can be made economically.

In addition to controlling the flow of fluid into the pressure-vessel and fluid-extraction assembly 18, the valve system 14 controls the flow of: (1) purging supercritical fluid from the space between the cartridge and interior of the vessel to the collector system 16 or to a vent; and (2) the extractant from the interior of the cartridge to the collector system 16 for separate collection.

To hold sample 134 during an extraction process, the pressure-vessel and fluid-extraction assembly 18 includes a heating block 22, a pressure vessel 24 and a cartridge and plug assembly 26 with the cartridge and plug assembly 26 extending into the pressure vessel 24. The pressure vessel 24 fits within the heating block 22 for easy assembly and disassembly. With this arrangement, the heating block 22 maintains the fluids within the pressure-vessel and fluid-extraction assembly 18 at supercritical fluid temperature and pressure for proper extraction.

The cartridge and plug assembly 26 includes an extraction cartridge assembly 30, a breech plug 32 and a knob 34 which are connected together so that: (1) the pressure vessel 24 is easily sealed with the breech plug 32; (2) the extraction cartridge assembly 30 snaps onto the breech plug 32 and the assembly may be carried by the knob 34; and (3) the knob 34 serves as a handle to insert and fasten the assembly to the tube pressure vessel with the extraction tube communicating with an outlet aligned with its axis and an inlet for the space between the internal walls of the pressure vessel 24 and the exterior of the extraction cartridge assembly 30 and for the interior of the extraction cartridge assembly 30 being provided through a groove circumscribing the assembly inside the pressure vessel 24.

With this arrangement the extraction cartridge assembly 30 may be easily sealed in the pressure vessel 24 by threading the breech plug 32 into it and may be easily removed by unthreading the breech plug 32 and lifting the knob 34. The extraction cartridge assembly 30 contains a hollow interior, an inlet and an outlet so that a sample to be extracted may be placed in the hollow interior and supercritical fluid passed through the inlet, the hollow interior and to the outlet to a collector. The extraction cartridge assembly 30 serves as an extraction chamber or tube, the pressure vessel 24 serves as an extraction vessel and the heating block 22 serves as an oven as these terms are commonly used in the prior art.

In the preferred embodiment, the knob 34 is of a low heat conductivity material and it should include in all embodiments at least a heat insulative thermal barrier located to reduce heating of the handle portion of the knob 34. It extends outside of the pressure vessel 24 and is adapted to aid in the sealing of the pressure vessel 24 and the breech plug 32 together so that the extraction cartridge assembly 30 is within the pressure vessel 24 for maintaining it at the appropriate temperature and the knob 34 is outside the pressure vessel 24 so as to remain cool enough to handle.

Although in the preferred embodiment the knob 34 is a heat insulative material, it only needs to be insulated against heat conducted from the interior of the pressure vessel 24 and this may also be done by a thermal barrier separating the pressure vessel 24 from the knob 34 such as an insulative disc having a width of at least 1 millimeter and extending across the cross-section of the knob 34 to the extent of at least 80 percent of the cross-section to effectively block any considerable amount of transfer of heat between the cartridge and the knob 34. It should have a heat conductivity no greater than 0.05 calories/cm. sec. degree C. at 30 degrees Centigrade.

The extraction cartridge assembly 30 has an opening which permits some supercritical fluid to enter the pressure vessel 24 to follow one path passing into the extraction tube and out through an outlet of the extraction tube into a conduit leading to a collector. Other supercritical fluid follows a second path around the outside of the cartridge to remove contaminants from the pressure vessel 24, equalize pressure and flow from another outlet. One of the inlet and outlet of the extraction cartridge assembly 30 enters along the central axis of the extraction cartridge assembly 30 and the other from the side to permit rotation of parts with respect to each other during seating of the pressure vessel 24 and yet permit communication of the extraction cartridge assembly 30 with the fluid source and with the collector. To reduce wasted heat and fluid, the space between the outside of the cartridge and the inside walls of the pressure vessel 24 is only large enough to accommodate the flow of purging fluid and to equalize pressure between the inside and outside of the cartridge. The volume between the outside of the cartridge and the inside of the pressure vessel 24 is less than 10 cubic centimeters.

In the preferred embodiment, the inlet opens into an annular space between the internal wall of the pressure vessel 24 and the cartridge and plug assembly 26. The fluid follows two paths from the annular space, both of which include an annular manifold with narrow holes and a passageway that communicates with the recess in the breech plug 32. One path opens into the extraction cartridge assembly 30. The other passes along the narrow space outside the extraction cartridge assembly 30. Thus, supercritical fluid enters the extraction tube through a labrythian like path and at the same time passes outside the extraction tube so that the pressure inside the extraction tube is always substantially the same as that inside the pressure vessel 24. Because the pressures are substantially the same, the tube itself may be formed of relatively inexpensive plastics notwithstanding that a high pressure is desirable for extraction from the sample within the extraction tube.

The pressure vessel 24 is generally formed of strong material such as metal and is shaped as a container with an open top, an inlet opening and two outlet openings. The inlet opening is sized to receive an inlet fitting 42, the inlet fitting 42 being shown in FIG. 1 connected in series with check valve 60A to corresponding heat exchanger 40. Each of the two outlet openings are sized to receive a different one of a corresponding purge valve fitting 44, and a corresponding extractant fluid fitting 46. With these fittings, the pressure vessel 24 is able to receive the cartridge and plug assembly 26 in its open end and permit communication between the cartridge and the extractant fluid fittings such as shown at 46. The inlet fittings such as shown at 42 and purge valve fitting, such as 44, permit communication with the inside of the pressure vessel 24.

To control the flow of fluids to and from the pressure vessel and fluid-extraction assembly 18, the valve system 14 includes an extractant valve 50, a purge fluid valve 52 and an extracting fluid valve 54.

To introduce extracting fluid into the pressure-vessel and fluid-extraction assembly 18, the extracting fluid valve 54 communicates with one branch of the tee joint 20 through tube 56 and with one end of the heat exchanger 40 through tube 58, the other end of the heat exchanger 40 communicating with the inlet fitting 42 through tube 60, check valve 60A and tube 60B. With these connections, the extracting fluid valve 54 controls the flow of fluid from the pumping system 12 through the heat exchanger 40 and the pressure vessel 24 through the inlet fitting 42.

To remove purge fluid from the pressure vessel 24, the purge fluid valve 52 communicates at one port with the purge valve fitting 44 through tube 62 and with its other port through tube 64 (not shown in FIG. 2) with the collector system 16A or with a vent (not shown) to remove fluid containing contaminants from the exterior of fluid extraction cartridge assembly 30 and the interior of the pressure vessel 24.

To remove extractant from the extraction cartridge assembly 30, the extractant valve 50 communicates at one of its ports through tube 66 with the extractant fluid fitting 46 and through its other port with the collector system 16A through tube 68 for the collecting of the extracted material, sometimes referred to as analyte or extractant, from the sample within the pressure vessel and fluid-extraction assembly 18.

For convenience, the valves 52 and 54 are mounted to be operated by a single manual control knob 70. To supply fluid to the valve system 14: (1) the tube 56 carries pressurized fluid from the pumping system 12 to tee joint 20; (2) tube 76 is connected to one arm of tee joint 20 to carry pressurized fluid to another liquid extraction system unit not shown on FIG. 1; and (3) the remaining arm of the tee joint 20 is connected through the tube 56 to an inlet valve 74 of extracting fluid valve 54. The valves 50, 52 and 54 are, in the preferred embodiment, SSi type 02-0120.

The extracting fluid valve 54 has a rotary control shaft 80 that is rotated to open and close its internal port. This shaft is operated by hand control knob 70 and carries spur gear 82 pinned to the control shaft 80. Spur gear 84, which is pinned to control shaft 107 of purge fluid valve 52, meshes with spur gear 82 so that when control knob 70 is rotated clockwise, extracting fluid valve 54 is closed, but since the control shaft 107 of purge fluid valve 52 is geared to turn in the opposite direction, the clockwise rotation of knob 70 opens purge fluid valve 52.

The relative locations of the two gears on the two shafts are such that, in the first (clockwise) position of the knob 70, the extracting fluid valve 54 is shut and the purge fluid valve 52 is open. Turning the control knob 70 counterclockwise 130 degrees from this first position opens extracting fluid valve 54 while allowing purge fluid valve 52 to remain open. Thus, both valves are open when the knob 70 is rotated 130 degrees counterclockwise from the first position. When the knob 70 is rotated 260 degrees counterclockwise from the first position, extraction fluid valve 54 is open and purge fluid valve 52 is shut. Thus, there are three definable positions for control knob 70: (1) clockwise with valve 54 shut and valve 52 open; (2) mid position with both valves open; and (3) full counterclockwise with valve 54 open and valve 52 shut.

The extractant valve 50 includes an inlet fitting 120, outlet fitting 122, manual control knob 132 and control shaft 126. The rotary control shaft 126 is attached to control knob 132. When the extractant valve 50 is opened by turning the control knob 132 counterclockwise from its closed position, fluid flows from the extraction cartridge assembly 30, through the extractant fluid fitting 46, the tube 66, the valve inlet fitting 120, the outlet fitting 122, through the tube 68 and into the collector system 16A.

The collector system 16A includes a purge coupling 90, a purge fluid collector 92, an extractant coupling 94, an analyzing instrument 96, and an extractant fluid collector 98. The purge fluid flowing through the valve 52, flows through purge coupling 90 into the capillary tube 110 and from there into the purge fluid collector 92 where it flows into a solvent 100. Similarly, the extractant flowing through extractant valve 50 flows through tube 68 to the extractant coupling 94 and from there to the capillary tube 128 and extractant fluid collector 98 which contains an appropriate solvent 104 in the preferred embodiment.

The analyzing instrument 96 may be coupled to the capillary tube 128 through an optical coupling 102 in a manner known in the art. The optical coupling 102 is a photodetector and light source on opposite sides of a portion of the capillary tube 128, which portion has been modified to pass light. This analyzing instrument 96 monitors extractant and may provide an indication of its passing into the extractant fluid collector 98 and information about its light absorbance. Other analytical instruments may also be used to identify or indicate other characteristics of the extractant.

While a simplified manual system for supercritical extraction has been described for simplicity, automatic systems may utilized the invention. A more detailed description of a manual system is disclosed in United States patent issued Mar. 10, 1992 and a more detailed description of an automatic system is provided in U.S. application Ser. No. 07/553,119, filed Jul. 13, 1990, for APPARATUS AND METHOD FOR SUPERCRITICAL FLUID EXTRACTION and U.S. application Ser. No. (18-438-15-1) filed concurrently with this application and assigned to the same assignee for APPARATUS AND METHOD FOR SUPERCRITICAL FLUID EXTRACTION. These United States applications are continuations in part of the aforesaid U.S. Pat. No. 5,094,753. The disclosures of the aforementioned patent and patent applications are incorporated herein by reference.

Figure 2:
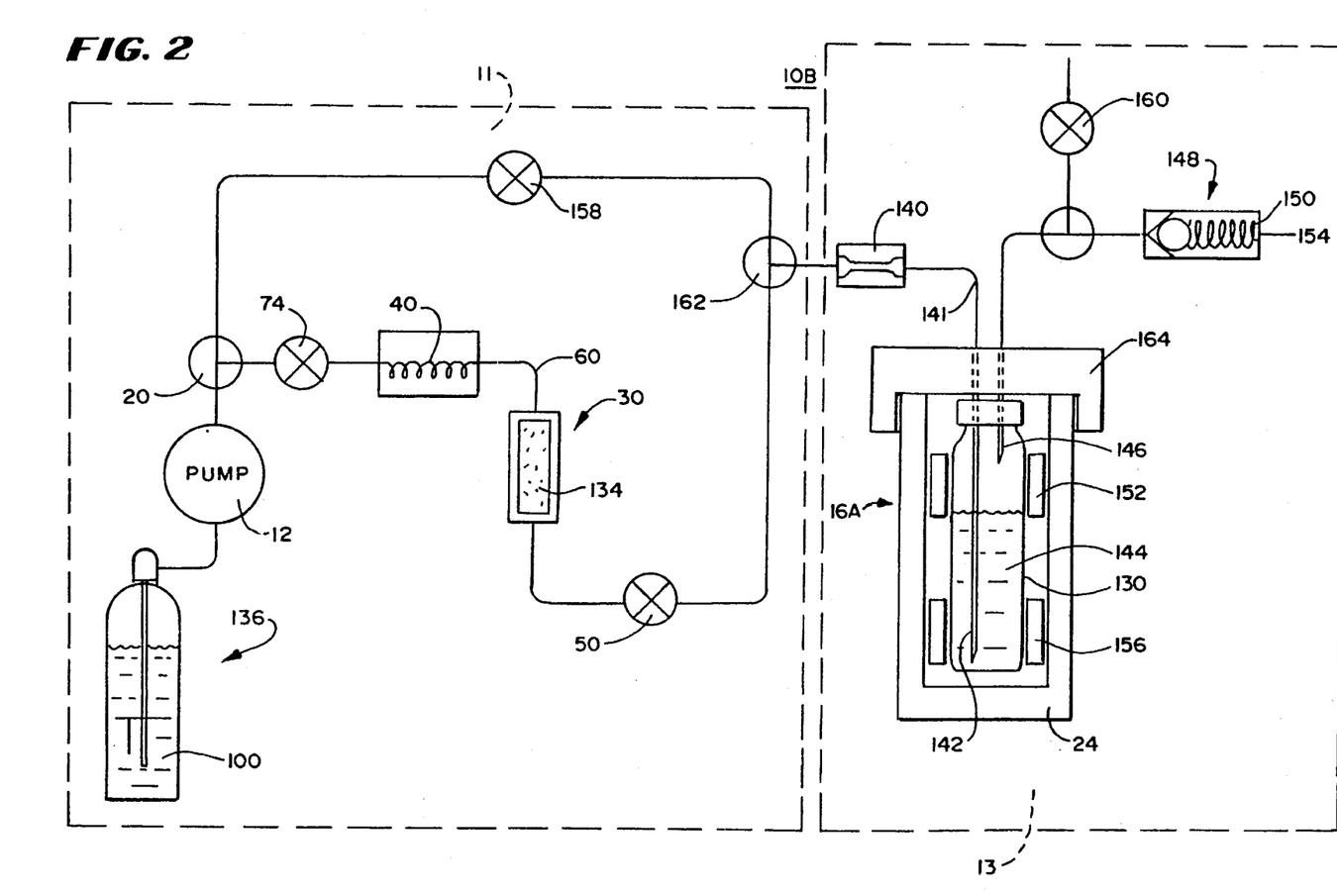
FIG. 2 is a schematic diagram of an extraction system utilizing a pressurized collection system.

In FIG. 2, there is shown a schematic diagram of an extraction system 10B having an extractor portion 11 and a collector portion 13. The extractor portion 11 extracts extract from samples and supplies extractant to the collector portion 13, usually at high temperatures and pressures. The extraction system includes as its principal components the source of extractant fluid 100, a pumping system 12, valves 74, 158 and 50, the extraction cartridge assembly 30 and the heat exchanger 40. These components are connected together to operate in the manner disclosed in the embodiment of FIG. 1 and as described in the aforementioned patent and patent applications for manual and automatic extraction systems.

In these systems, extraction solvent reservoir 136 feeds the solvent through a delivery pumping system 12. The pressure and temperature of the solvent stream are raised to the supercritical state by pump 12 and heat exchanger 40 and supplied to sample 134 in the extraction cartridge 134. The supercritical solvent removes the analyte from the sample matrix as it is carried through the extraction chamber 30.

A flow control pressure restrictor 140 in the collection portion 13 maintains the desired extraction conditions in the extraction cartridge assembly 30 while reducing the extract pressure for collection.

The collection portion 13 includes as its principal parts, a transfer tube 141, a dip tube 142, a pressure vessel 24, a collection vessel 130, a vent tube 146 and the heaters 152 and 156. The transfer tube 141, restrictor 140 and dip tube 142 are in series and carry the liquid extract into the collection vessel 130. The collection vessel 130 is positioned within the pressure vessel 24 adjacent to the heaters 152 and 156 to be heated thereby. The vent tube 146 extends into the collection vessel 130 and may vent through the check valve 148 and valve 160.

In one embodiment, the flow control pressure restrictor 140, transfer tube 141, and dip tube 142, may be one and the same, releasing pressure directly into collection solvent 144.

In another embodiment, the extraction restrictor 140 is located at the lower end of dip tube 142, maintaining the extract at extraction pressure until it reaches the collection solvent 144.

The collection solvent 144 is a mixture of the extraction solvent 100, extracted analyte, and a secondary liquid solvent which is present to carry the analyte after the extraction solvent 100 has been removed. The secondary liquid solvent is optional for the practice of this invention but is often necessary to transfer the analyte to the analysis means.

When the extraction solvent 100 vaporizes, it exits the collection vessel 130 through the vent tube 146. The vent restrictor 148 is a pressure control restrictor which maintains the pressure vessel 24 and collection vessel 130 at a pressure selected for optimum separation of the extraction solvent 100 from the collection solvent 144. Selection of pressure also determines the temperature in collection vessel 130 because of the vapor pressure-temperature characteristics of the extraction solvent 100.

The vent restrictor 148 may be any of a type of spring force regulated back-pressure control valves such as the Haskel model 156570-1 (Haskel, Inc. Burbank, Calif. 91502, USA). A spring 150 applies a force to offset the pressure it is regulating.

When the force generated by the regulated pressure exceeds the spring force, an orifice is opened to allow gas to flow through the valve. The spring force and therefore the pressure, can be manually or automatically controlled. Controlling the collection solvent pressure also controls its temperature.

The optimal fractional evaporation of extraction solvent 100 is achieved when the ratio of extraction solvent vapor pressure to analyte vapor pressure is as high as possible. This ratio will typically increase as the temperature decreases with the result that the optimum temperature is very low and limited by the vapor pressure-temperature characteristic of the supercritical solvent or the freezing point of the solvents or extracts.

In the embodiment of FIG. 2, there are two vessels in the collection system with a strong outer high pressure vessel 24 supporting a removable weaker internal collection vessel 130. However, the extraction can be implemented with a single pressure vessel designed to safely contain the maximum expected collection pressure. This arrangement enables extracts to be collected at high pressure using less expensive, removable, replaceable, lower pressure vessels by creating pressure between the two pressure vessels so that the inner vessel is only stressed by the pressure differential rather than the higher absolute pressure.

It is desirable to collect the fluid from each extraction in a clean vessel to prevent carryover from one extraction to the next. A high pressure vessel capable of containing collection pressures is expensive relative to commonly available low pressure vessels, such as laboratory glassware. For illustration, FIG. 1 shows a relatively weak glass EPA sample vial as the removable low pressure collection vessel 130. The collection vessel size may range from GC vials which contain about one milliliter to vessels larger than the sample cartridge 30. Large vessels may be necessary if the sample contains a large percentage of extractables.

To allow the use of such low cost, easily cleaned collection vessels, the collection pressure is contained by the outer high pressure vessel 24. The gas in the pressure vessel 24 may communicate with the gas in collection vessel 130 by a nonrestrictive path inside the pressure vessel 24 around the periphery of either of tubes 146 or 142.

In this way, the pressure outside the collection vessel 130 equals the pressure inside the collection vessel 130. Because the collection vessel 130 does not support a pressure differential equal to the difference between the collection pressure and atmospheric pressure, a low cost, weaker vessel such as thin glassware can be used. In the preferred embodiment, the pressure supported by the inner collection vessel is zero since the pressure outside the inner vessel 130 equals the pressure inside this vessel.

In this embodiments a temperature differential is established vertically through the wall of the collection vessel 130. It is easier to maintain this temperature differential through a thin wall. Thus, in addition to being more cost effective because it has low pressure holding capacity, it has an advantage of reaching temperature equilibrium faster.

The collection and extraction solvent mixture level in the collection vessel 130 must be controlled to prevent overflow of the collection vessel 130. It is also desirable to maintain the collection solvent 144 above a minimum level to encourage mixing with the extract. This liquid level control is provided by placing a vertical temperature differential on the wall of the collection vessel 130 at the desired liquid level.

The top portion of the collection vessel 130 is maintained at a temperature higher than the bottom portion by action of the heater 152. The upper temperature is chosen based on the vapor pressure of the extraction solvent to be evaporated. The temperature of the upper wall is set high enough that extraction solvent at that temperature has a vapor pressure higher than that established by the vent restrictor 148.

The temperature of the extraction solvent 100 and the collection solvent 144 is controlled by the pressure setpoint of the vent restrictor 148. During the extraction, the lower portion of the collection vessel 130 is effectively insulated from heat flow. The heater 152 is turned off and is only in thermal contact with the wall of collection vessel 130.

With little heat flow into the solvents, the solvent level rises towards heater 152 as extract is continually added from the extraction chamber 30. When the extraction solvent evaporates, the heat of vaporization loss cools the collection solvent 144, retarding further evaporation. When the collection solvent mixture reaches the level of the upper hot zone established by heater 152, contact with the heated wall raises the collection solvent surface temperature and pressure to a level that is greater than the pressure at which the vent restrictor 148 opens.

Vaporized extraction solvent then evaporates from the collection vessel 130 and exits the vent restrictor 148 through the vent 154. Evaporation continues until the mixed collection solvent and liquified extraction solvent level drops low enough to reduce heat flow into the mixture.

In practice, with extract continually flowing into the collection vessel 130, a balance is established. The mixed collection solvent and extraction solvent level is just high enough to provide heat flow sufficient to vaporize extraction solvent at the extraction flow rate. The collection solvent is not vaporized because it has a significantly lower vapor pressure.

The extraction continues to completion with both the collection solvent volume conserved and temperature regulated. It is desirable to control both of these parameters. The collection solvent/extraction solvent mixture temperature is usually chosen to be as low as possible to optimize the fractional evaporation efficiency but just high enough to prevent freezing of solvents or extracted compounds such as water.

The liquid collection solvent is often a relatively volatile compound. Conventional liquid trapping is often plagued by loss of the collection solvent during the extraction. It is not unusual to lose all the collection solvent before the extraction is complete. In this case, collection solvent must be added to the collection vessel during the extraction, which complicates the system or requires operator monitoring and intervention. This is a problem in particular for automatic extraction systems.

The collection solvent volume regulation inherent in this invention solves this problem. Any collection solvent loss is automatically replaced by extraction solvent flowing from the extraction chamber 30 which in most cases performs adequately as a collection solvent. In addition, the loss of volatile analytes or collection solvent 144 is inhibited by the gas pressure over the collection solvent mixture.

At the same extraction solvent evaporation rate, the pressurized collection system loses dramatically less volatile compounds to evaporation than a conventional atmospheric pressure liquid trap does. This method of fractional evaporation allows efficient trapping of compounds with much higher volatility than was previously possible.

A test extraction was done with an apparatus of the type described in this disclosure. Gasoline was spiked onto an inert matrix and extracted with carbon dioxide to test collection efficiency. The analytes were collected in 0.5 ml of methylene chloride in a 1.5 ml GC collection vial without collection solvent replenishment. The collection solvent mixture was kept in the liquid state under 100 psi pressure and reduced temperature.

During extraction carbon dioxide was vaporized from the collection vial by fractional evaporation with a dual temperature zone collection vessel. Evaporation continued after extraction until the carbon dioxide was removed from the collection vial.

BTEX recoveries by GC analysis were:

86.3% of Benzene 95.4% of Toluene 97.1% of Ethylbenzene 97.2% of m,p-Xylene 98.1% of o-xylene While two electrical heaters 152 and 156 are used in the preferred embodiment, similar means can be employed to create the dual temperature zone collection solvent level control. For example, a heated probe or rod can be inserted into the collection vessel 130 from the top with the probe tip at the desired fluid level. The heat of vaporization then flows from the probe into the collection solvent 144 when the solvent level reaches the probe tip increasing vapor pressure.

Instead of relying on the locations of heaters, the level of liquid may be monitored and heat applied when the level exceeds a predetermined level. More specifically, the fluid level may be measured or monitored in the collection vessel 130 and sufficient heat may be applied to the collection solvent 144 in a manner as to control the liquid level. The location of heat flow into the collection solvent is not critical. The level monitoring can be done optically or by other means known in the art of fluid level control.

For example, a light can be transmitted through a glass or other transparent collection vessel at the desired collection solvent level and the transmitted light sensed on the opposite side. When the collection solvent level rises above the light level, the light will be bent or otherwise distorted sufficiently so that the decrease in light transmission will indicate presence of fluid.

After the extraction is complete, it is necessary to remove the remaining extraction solvent from the collection vessel 130. This is done by evaporation. Heat is applied to the lower portion of the collection vessel 130 by concentration heater 156. If the volume of extraction solvent 100 in the collection vessel 130 is small, heat flowing vertically through the vessel wall from the level control heater 152 and from the surrounding gas or air may be sufficient.

When the extraction solvent is evaporated, this leaves the extract dissolved in the collection solvent in vessel 130. Residual pressure is vented by opening the outlet valve 160, and pressure vessel 24 is unscrewed from vessel cap 164. Collection vessel 130 may then be removed.

An example is collection in a small volume GC vial where most of the collection solvent volume is taken up by the collection solvent which is not evaporated. In this case, the concentration heater 156 may not be required. The analytes are concentrated in the collection solvent 144 if present, or deposited in the collection vessel 130 without collection solvent. A primary reason for the reduction of the amount of collection solvent is to reduce the use of hazardous organic solvents.

This invention allows practical liquid trapping in solvents such as carbon dioxide which are safe, nontoxic, easy to evaporate and easy to dispose of. If the analytes are not greatly volatile, liquid trapping in the extraction solvent provides excellent results without the use of hazardous solvents. If the analytes are quite volatile, the collection solvent may be necessary to dissolve the analytes and provide a carrier solvent for the analysis.

Because the fractional evaporation efficiency is temperature dependent, it is desired to cool the collection solvent 100 before beginning the extraction if the analytes are volatile. Also, if the extraction solvent 100 is to be the collection solvent 144, some solvent should be transferred to the collection vessel 130 before the extraction is begun. To achieve both the pre-cooling and collection solvent tranfer, a bypass valve 158 provides an alternate path for extraction solvent flow from the pumping system 12 to the flow control pressure restrictor 140.

As extraction solvent 100 is pumped directly to the collection vessel 130, a volume of extraction solvent will evaporate, sufficient to cool the collection solvent 130 to the desired collection temperature as determined by the pressure setpoint of the vent restrictor 148. Other means can be employed to cool the collection solvent 144 such as mechanical refrigeration, thermoelectric devices, or other cooling means known in the art.

In operation, an extraction cycle starts with the bypass valve 158, the extraction valve 50, and the vent valve 160 all closed. The inlet valve 74 is opened and the pump 12 operated to pressurize the extraction chamber 30. The bypass valve 158 is opened to pass clean extraction solvent 100 from pumping system 12, through tee joint 20, bypass valve 158, tee joint 162 and extraction restrictor 140 into the collection vessel 130.

When the collection solvent 144 is at the desired temperature and volume, the bypass valve 158 is closed. After the extraction chamber 30 is pressurized and after any desired static extraction time has elapsed, the extraction valve 50 is opened. Extraction solvent 100 flows from the pump 12, through tee joint 20, solvent heater 40, into extraction chamber 30 and through sample 134 where the analytes are solvated.

The extract fluid then flows through extraction valve 50, tee joint 162, flow control pressure restrictor 140 and into collection vessel 130. Extraction proceeds with the collection solvent 144 level controlled as described earlier. Extraction solvent is continually evaporated from the collection solvent 144 throughout the extraction and exits the collection vessel 130 through vent tube 146 which originates in the vapor space above the collection solvent 144. The extraction solvent vapor passes through vent restrictor 148 and out vent 154. When the extraction is complete, extraction valve 50 is closed. Evaporation of extraction fluid continues after extraction until it is fully removed from the collection vessel 130. This concentration step may require use of the concentration heater 156 as described above.

After the liquid extraction solvent 100 has been evaporated from the collection vessel 130, the vent valve 160 is opened to equalize the gas pressure inside and outside the pressure vessel 24. The pressure vessel cap 164 is removed and the collection vessel 130 is exchanged with a clean vessel for the next extraction. The pressure vessel cap 164 is replaced and the vent valve 160 is closed. The collection vessel loading and unloading can be automated by a mechanized means in an automated system.

This technique can be adapted to trapping the analyte while the extraction solvent is released by spraying the extractant onto a cold surface or solid sorbent maintained at an elevated pressure throughout the extraction, followed by a secondary solvent rinse to remove the analyte. The trapping surface typically consists of small metal or glass beads chosen for inertness and low surface energy. Such beads are located in pressurized, cold collecting vessel 130.

In such an adaption, the secondary liquid solvent is used to rinse, wash or remove the analyte from the trapping surface after vessel 130 is removed from the pressure vessel as described earlier. Such washing may be carried out by any appropriate concentrated means. The washing product may be collected in a small vial and separated by gas chromatography. Thus, the trapping material may be chosen for trapping characteristics without excessive loss of extracts in vaporization procedures because of the ability to trap under pressure, to use a selected solvent applied under pressure in the collection vessel and to concentrate extract in it under pressure. Thus, loss of extract because of vaporization or failure to deposit in the trap may be minizied.

By treating the separation as a fractional evaporation, extract plus extraction fluid is kept in the liquid state under elevated pressure, mixed with the collection solvent if present. The extraction solvent is then vaporized in the manner of a fractional evaporation. The most common extraction solvent, carbon dioxide, cannot be maintained in the liquid state at atmospheric pressure. If the separation of extraction solvent from analyte is to be done as fractional evaporation, it must be done at a pressure sufficient to keep the extraction solvent liquid. In the case of carbon dioxide, this requires about five atmospheres of pressure, which is possible in the collection vessel 130.

As can be understood from the above description, the supercritical extraction technique has several advantages, such as for example: (1) it provides good trapping efficiency; (2) it provides low extract/solvent losses; (3) it provides reduced freezing and plugging of the restrictor; (4) it reduces icing up of the outside of the vial; (5) it permits the conditions of the extraction, such as temperature and pressure, to be changed such as to remove certain substances from the sample matrix and deposit each substance in a separate vial; and (6) it provides efficient trapping of high vapor pressure analytes.

More specifically, this technique has the advantages of: (1) minimizing the decrease of the solvent power which prevents analyte loss in the transfer step by transferring the extraction solvent mixed with analyte to the collection vessel under pressure; (2) minimizing evaporation loss of the analyte and collection solvent if present by separating the extraction solvent from the analyte or analyte plus collection solvent by fractional evaporation; (3) enabling volatile collection solvents to be used without a need for collection solvent replenishment during the extraction; (4) reducing the size of the gas bubbles which form as the extraction solvent expands and thus causing boiling to be less violent by fractional evaporation under pressure; and (5) permitting in one embodiment, transfer of the extract to a collection vessel without passing it through a restrictor because only the evaporated extraction solvent and, in some cases, evaporated collection solvent passes through a pressure release or restrictive element and the extraction solvent is maintained at extraction conditions throughout the transfer step so as to prevent restrictor plugging and simplify the restrictor design with no need for restrictor heating.

Although a preferred embodiment of the invention has been described in some detail, many modifications and variations of the preferred embodiment can be made without deviating from the invention. Therefore, it is to be understood that within the scope of the appended claims the invention may be practiced other than as specifically described.

What is claimed is:

1. An apparatus for supercritical fluid extraction comprising:

a supercritical fluid extractor;

at least one container arranged to collect extractant and extraction solvent from said supercritical fluid extractor;

means for pressurizing the at least one container at a predetermined pressure wherein extractant selectively passes into collection solvent in the at least one container; and means for selectively and substantially continuously removing extraction solvent from said collection solvent in said at least one container based on vapor pressure differential between the extraction and collection solvents.

2. An apparatus for supercritical fluid extraction in accordance with claim 1 further comprising a device for controlling the pressure within the at least one container.

3. An apparatus for supercritical fluid extraction in accordance with claim 2 further comprising separating means for separating fractional evaporated extraction solvent from liquid collection solvent mixed with thereof in the removed solvent by separating liquid and gas phases.

4. An apparatus for supercritical fluid extraction comprising:

a supercritical fluid extractor means;

at least one container arranged to collect extractant and extraction solvent from said extractor means;

means for pressurizing the at least one container at a predetermined pressure wherein extractant selectively passes into collection solvent in the at least one container;

means for selectively and substantially continuously removing extraction solvent from said collection solvent in said at least one container based on vapor pressure differential between the extraction and collection solvent during extraction;

each said at least one container being adapted to communicate with said supercritical fluid extraction means by means of a restrictor; and each said at least one container having an opening with said opening being closed by a septum means which at least partially seals the container when the container is not in contact with the restrictor.

* * * * *